United States Patent
Oya et al.

(10) Patent No.: US 7,972,488 B2
(45) Date of Patent: Jul. 5, 2011

(54) SENSOR DETERIORATION JUDGING APPARATUS AND SENSOR DETERIORATION JUDGING METHOD

(75) Inventors: Seiji Oya, Aichi (JP); Tomohiro Wakazono, Kounan (JP); Koji Shiotani, Kasugai (JP); Tomonori Kondo, Kounan (JP); Mineji Nasu, Kounan (JP); Hiroshi Kubota, Wako (JP); Kazuo Yanada, Wato (JP); Koichi Awano, Wako (JP)

(73) Assignees: NGK Spark Plug Co., Ltd, Aichi (JP); Honda Motor Co., Ltd, Tokyo (JP)

( * ) Notice: Subject to any disclaimer, the term of this patent is extended or adjusted under 35 U.S.C. 154(b) by 1015 days.

(21) Appl. No.: 11/602,983

(22) Filed: Nov. 22, 2006

(65) Prior Publication Data
US 2007/0119708 A1     May 31, 2007

(30) Foreign Application Priority Data
Nov. 25, 2005   (JP) ................ P2005-340536

(51) Int. Cl.
G01N 27/417     (2006.01)
(52) U.S. Cl. .............. 204/424; 204/427; 205/784.5; 205/784; 73/23.31; 73/23.32
(58) Field of Classification Search .......... 204/421–429; 205/780.5–781, 782, 783.5–785.5; 73/23.31–23.32
See application file for complete search history.

(56) References Cited

U.S. PATENT DOCUMENTS

| | | | | |
|---|---|---|---|---|
| 4,753,203 A | * | 6/1988 | Yamada | 73/23.32 |
| 4,938,194 A | * | 7/1990 | Kato et al. | 123/688 |
| 6,120,663 A | * | 9/2000 | Kato et al. | 204/401 |
| 2004/0238378 A1 | | 12/2004 | Kumazawa et al. | |

FOREIGN PATENT DOCUMENTS

| | | | |
|---|---|---|---|
| JP | 11-14589 | | 1/1999 |
| JP | 2002257777 A | * | 9/2002 |
| WO | 03/083465 | | 10/2003 |

OTHER PUBLICATIONS

Machine English Translation of JP 2002-257777A.*
"Ratio." Merriam-Websters Online Dictionary. Merriam-Webster. Web. Feb. 26, 2010. <http://www.merriam-webster.com/medical/ratio>.*

* cited by examiner

Primary Examiner — Nam X Nguyen
Assistant Examiner — Bach T Dinh
(74) Attorney, Agent, or Firm — Morgan, Lewis & Bockius LLP

(57) ABSTRACT

In a sensor diagnosis process, a controller for controlling an NOx gas sensor performs processing of changing the oxygen partial pressure in a second measurement chamber by changing the oxygen partial pressure in a first measurement chamber (S190), processing of detecting a current flowing through a second pump cell before the change of the oxygen partial pressure (S180), and processing of detecting a current flowing through the second pump cell after the change of the oxygen partial pressure (S230). Furthermore, the controller performs processing of judging whether or not the ratio between the current values detected by the respective current detecting unit falls within an allowable range, judging that the second pump cell 113 is in a normal state if the ratio between the current values falls within the allowable range, and judging that the second pump cell 113 is in a deteriorated state if the ratio between the current values is out of the allowable range (S240 and S250).

5 Claims, 3 Drawing Sheets

SENSOR DETERIORATION JUDGING APPARATUS AND SENSOR DETERIORATION JUDGING METHOD

BACKGROUND OF THE INVENTION

1. Field of the Invention

The present invention relates to a sensor deterioration judging apparatus and a sensor deterioration judging method for judging whether a gas sensor is in a deteriorated state.

2. Description of the Related Art

A gas sensor is known which is equipped with a first measurement chamber, a first oxygen ion pump cell, a second measurement chamber, a second oxygen ion pump cell, a reference oxygen chamber, and an oxygen partial pressure detection cell.

Various apparatus for judging the state of such a gas sensor have been proposed which measure currents flowing through various cells of the gas sensor, output voltages of cells, impedances of cells, or like parameters and detects a failure state of the gas sensor on the basis of whether or not measurement results are within allowable ranges (refer to JP-A-11-014589 (corresponding to U.S. Pat. No. 6,120,663) and WO-A-03/083465 (corresponding to US 2004/0238378 A1), for example).

3. Problems to be Solved by the Invention

However, the above conventional apparatus have a problem that they cannot detect a deteriorated state of a gas sensor such as low sensitivity of a cell though they can detect fatal failure states such as a line disconnection and short-circuiting among various states of a gas sensor.

In a gas sensor having a fatal failure, the values of currents, voltages, impedances, etc. of various cells are clearly out of the ranges of those of a normal gas sensor. Therefore, a failure state of a gas sensor can be detected by the above conventional apparatus.

In contrast, in a deteriorated gas sensor, the values of currents, voltages, impedances, etc. of various cells are approximately in the same ranges as those of a normal gas sensor. Therefore, it is difficult to discriminate a deteriorated state from a normal state on the basis of the above values. Therefore, it is difficult for the above conventional apparatus to detect a deteriorated state of a gas sensor.

Having a different a gas detection characteristic than in a normal state, a gas sensor in a deteriorated state cannot produce the same gas detection result as in the normal state and hence may be lowered in gas detection accuracy.

The present invention has been made in view of the above problem, and an object of the invention is to provide a sensor deterioration judging apparatus and a sensor deterioration judging method capable of judging whether a gas sensor having various cells is in a deteriorated state.

SUMMARY OF THE INVENTION

The invention, which has been made to attain the above object, provides a sensor deterioration judging apparatus for judging whether a gas sensor is in a deteriorated state, the gas sensor including:

a first measurement chamber into which a gas to be measured is introduced through a first diffusion resistor portion;

a first oxygen ion pump cell having a first oxygen on conductor and first and second electrodes provided on the first oxygen ion conductor wherein the first electrode is arranged in the first measurement chamber which pumps oxygen into or out of the gas that has been introduced into the first measurement chamber to be measured;

a second measurement chamber in which the gas to be measured is introduced through a second diffusion resistor portion after being subjected to oxygen pumping in the first measurement chamber;

a second oxygen ion pump cell having a second oxygen ion conductor and third and forth electrodes provided on the second oxygen ion conductor wherein the third electrode is arranged in the second measurement chamber so that a current corresponding to a concentration of the gas to be measured in the second measurement chamber flows in the second oxygen ion pump cell;

a reference oxygen chamber set to have a reference oxygen partial pressure atmosphere; and an oxygen partial pressure detection cell having a third oxygen ion conductor and fifth and sixth electrodes provided on the third oxygen ion conductor so that the fifth electrode is provided in the first measurement chamber and the sixth electrode is provided in the reference oxygen chamber, the sensor deterioration judging apparatus comprising:

an oxygen partial pressure changing unit for changing an oxygen partial pressure in the second measurement chamber by changing an oxygen partial pressure in the first measurement chamber;

a first pump current detecting unit for detecting a current flowing through the second oxygen ion pump cell before the oxygen pressure changing unit changes the oxygen partial pressure;

a second pump current detecting unit for detecting a current flowing through the second oxygen ion pump cell after the change of the oxygen partial pressure by the oxygen partial pressure changing unit; and a deterioration judging unit for judging that the second oxygen ion pump cell is in a deteriorated state when a ratio between the currents detected by the first and second current detecting unit is out of a preset range.

The invention, which has been made to attain the above object, also provides a sensor deterioration judging method for judging whether the same gas sensor as recited above is in a deteriorated state, characterized by comprising the steps of detecting a current flowing through the second oxygen ion pump cell; changing an oxygen partial pressure in the second measurement chamber by changing an oxygen partial pressure in the first measurement chamber; detecting a current flowing through the second oxygen ion pump cell again after the change of the oxygen partial pressure in the first measurement chamber; and judging that the second oxygen ion pump cell is in a deteriorated state if a ratio between the detected currents is out of a preset range.

In the gas sensor as a subject of deterioration judgment, if the second oxygen ion pump cell is in a normal state (i.e., not in a deteriorated state), after a change of the oxygen partial pressure the current flowing through the second oxygen ion pump cell should vary from a current detected before the change of the oxygen partial pressure by an amount corresponding to a changed oxygen partial pressure. However, if the second oxygen ion pump cell is in a deteriorated state, after a change of the oxygen partial pressure the current varies by a smaller amount than in a normal state. For example, when the oxygen partial pressure is increased, only a current smaller than a normal-state current flows. That is, the ratio between current values detected before and after the change of the oxygen partial pressure goes out of the preset range.

Utilizing the above phenomenon, in the invention, currents flowing through the second oxygen ion pump cell before and after changing the oxygen partial pressure in the second measurement chamber are detected and whether the second oxygen ion pump cell is in a normal state is judged on the basis of whether or not the ratio between the detected currents falls within the allowable range.

Therefore, the above-described sensor deterioration judging apparatus and sensor deterioration judging method can judge whether or not the second oxygen ion pump cell is in a deteriorated state, and hence can judge whether or not the gas sensor having the various cells is in a deteriorated state.

Next, in the sensor deterioration judging apparatus, it is desirable that the oxygen partial pressure changing unit change the oxygen partial pressure in the second measurement chamber by changing an amount per unit time by which oxygen is pumped in or out by the first oxygen ion pump.

In this sensor deterioration judging apparatus, since the oxygen partial pressure changing unit changes the oxygen partial pressure in the second measurement chamber using the first oxygen ion pump cell, the oxygen partial pressure in the second measurement chamber can be changed without the need for newly disposing an oxygen pump cell for changing the oxygen partial pressure. Therefore, the structure for changing the oxygen partial pressure can be simplified.

Incidentally, in the sensor deterioration judging apparatus, it may take a certain time for the oxygen partial pressure in the second measurement chamber to become stable after the oxygen partial pressure in the first measurement chamber is changed by the oxygen partial pressure changing unit.

Therefore, in the above sensor deterioration judging apparatus, it is desirable that, as recited above, the second current detecting unit detect a current after the stabilization standby time (which is necessary for stabilization of the oxygen partial pressure in the second measurement chamber) has elapsed after the oxygen partial pressure changing unit changes the oxygen partial pressure in the first measurement chamber.

As described above, after the stabilization standby time has elapsed since a change of the oxygen partial pressure, the oxygen partial pressure in the second measurement chamber can reliably be set equivalent to that in the first measurement chamber. Therefore, whether or not the second oxygen ion pump cell is in a deteriorated state can be judged with higher accuracy by the deterioration judging unit.

Capable of judging, with higher accuracy, whether or not the second oxygen ion pump cell is in a deteriorated state, the above sensor deterioration judging apparatus can increase the judgment accuracy in judging whether the gas sensor is in a deteriorated state.

DESCRIPTION OF REFERENCE NUMERALS

Figure 1:
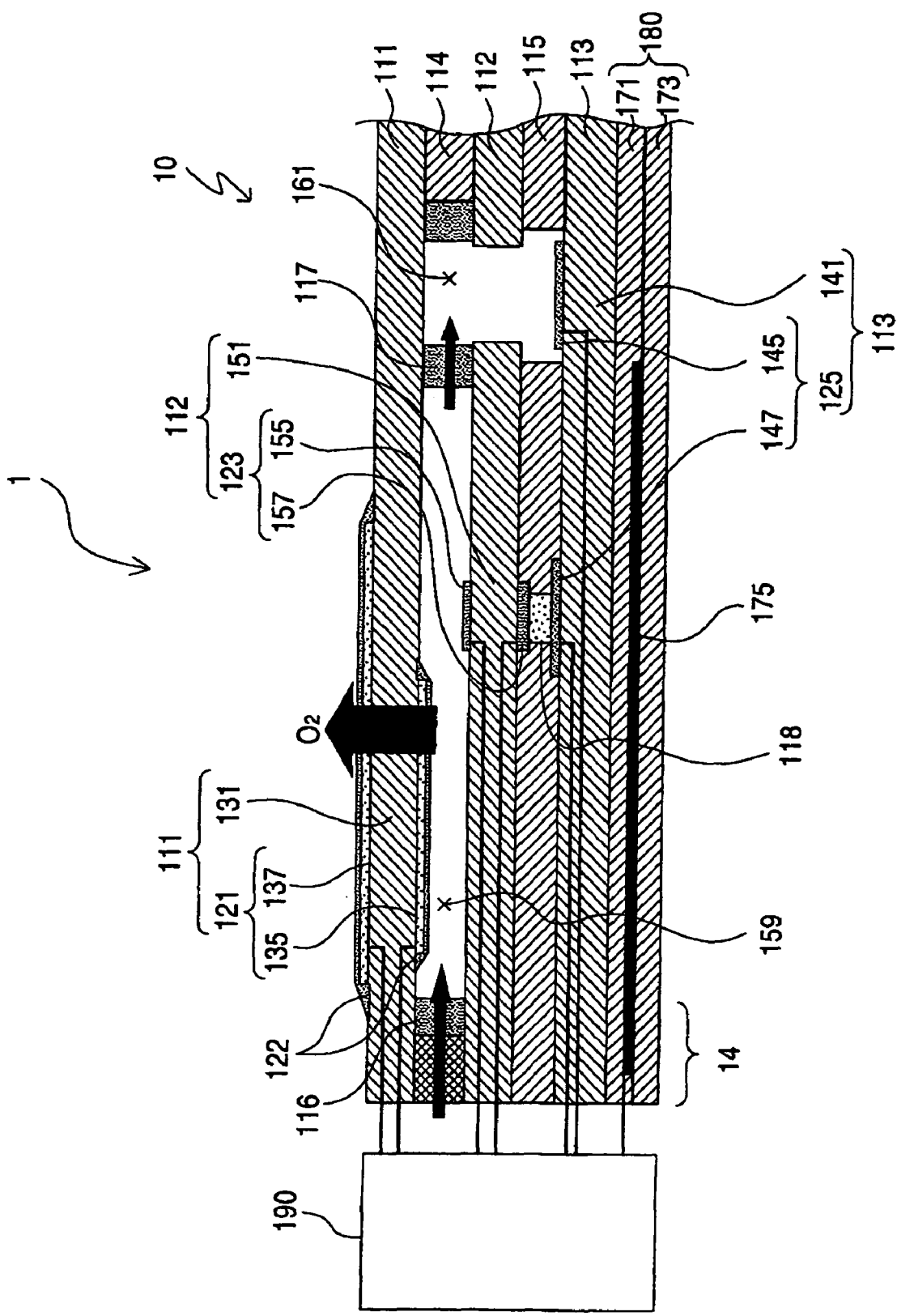
FIG. 1 shows the internal configuration of an NOx gas sensor.

Reference numerals used to identify various structural features in the drawings include the following.

10 . . . NOx gas sensor; 14 . . . Introduction passage; 111 . . . First pump cell; 112 . . . Oxygen partial pressure detection cell; 113 . . . Second pump cell; 114 . . . Insulating layer; 115 . . . Insulating layer; 116 . . . First diffusion resistor; 117 . . . Second diffusion resistor; 118 . . . Reference oxygen chamber; 121 . . . First porous electrodes; 122 . . . Protective layer; 123 . . . Detection porous electrodes; 125 . . . Second porous electrodes; 131 . . . First solid electrolyte layer; 135 . . . First electrode; 137 . . . Second electrode; 141 . . . Second solid electrolyte layer; 145 . . . Third electrode; 147 . . . Fourth electrode; 151 . . . Third solid electrolyte layer; 155 . . . Detection electrode (Fifth electrode); 157 . . . Reference electrode (Sixth electrode); 159 . . . First measurement chamber; 161 . . . Second measurement chamber; 171, 173 . . . Insulating layer; 175 . . . Heater; 180 . . . Heater unit; 190 . . . Gas sensor controller.

DETAILED DESCRIPTION OF THE INVENTION

An embodiment of the present invention will be hereinafter described with reference to the drawings.

FIG. 1 schematically shows the configuration of a gas detecting apparatus 1 having a gas sensor controller 190 to which the invention is applied.

The gas detecting apparatus 1 is equipped with the gas sensor controller 190 and an NOx gas sensor 10, and is used for, for example, the purpose of detecting a particular gas (in this embodiment, NOx) contained in an exhaust gas of various combustion apparatus such as an automobile internal combustion engine and a boiler.

The gas sensor controller 190 has, as a main component, a microcomputer that is equipped with a central processing unit (CPU), a RAM, a ROM, a signal input/output section, etc. The gas sensor controller 190 performs processing of drive-controlling the NOx gas sensor 10, processing of detecting the particular gas contained in an exhaust gas on the basis of a detection signal of the NOx gas sensor 10, sensor diagnosis processing (on-board diagnosis (OBD)) of judging whether the NOx gas sensor 10 is in a deteriorated state, and other processing.

In FIG. 1, the NOx gas sensor 10 is drawn as a sectional view showing its internal configuration. In the following description, the left-hand side and the right-hand side of the NOx gas sensor 10 will be referred to as "tip side" and "rear side," respectively. FIG. 1 shows the internal configuration of a tip-side portion of the NOx gas sensor 10, that is, its rear-side portion is omitted in FIG. 1.

First, the NOx gas sensor 10 will be described.

The NOx gas sensor 10 is configured in such a manner that a first pump cell 111, an oxygen partial pressure detection cell 112, and a second pump cell 113 are laid one on another via insulating layers 114 and 115 which are mainly made of alumina. In the NOx gas sensor 10, a heater unit 180 is laid on the second pump cell 113 on the side opposite to the cells 111 and 112.

Among the cells 111-113, the first pump cell 111 is composed of a first solid electrolyte layer 131 made of zirconia which is oxygen-ion-conductive and a pair of first porous electrodes 121 that are a first electrode 135 and a second electrode 137 between which the first solid electrolyte layer 131 is sandwiched. Each of the first electrode 135 and the second electrode 137 is made of platinum, a platinum alloy, cermet which contains platinum and ceramics (e.g., a solid electrolyte), or a like material. A protective layer 122 made of a porous material is formed on the surface of each of the first electrode 135 and the second electrode 137.

The second pump cell 113 is composed of a second solid electrolyte layer 141 made of zirconia which is oxygen-ion-conductive and a pair of second porous electrodes 125 that are a third electrode 145 and a fourth electrode 147 which are formed on that surface of the second solid electrolyte layer 141 which faces the insulating layer 115.

Each of the third electrode 145 and the fourth electrode 147 is made of platinum, a platinum alloy, cermet which contains platinum and ceramics (e.g., a solid electrolyte), or a like material.

The oxygen partial pressure detection cell 112 is composed of a third solid electrolyte layer 151 made of zirconia which is oxygen-ion-conductive and a pair of detection porous electrodes 123 that are a detection electrode (fifth electrode) 155 and a reference electrode (sixth electrode) 157 between which the third solid electrolyte layer 151 is sandwiched. Each of the detection electrode 155 and the reference electrode 157 is made of platinum, a platinum alloy, cermet which contains platinum and ceramics (e.g., a solid electrolyte), or a like material.

A first measurement chamber 159 into which a gas to be measured is to be introduced is formed inside the NOx gas sensor 10. A gas to be measured is introduced externally into the first measurement chamber 159 through a first diffusion resistor 116 which is disposed between the first pump cell 111 and the oxygen partial pressure detection cell 112.

The first diffusion resistor 116 is made of a porous material and disposed in a gas to be measured introduction passage 14 extending from the tip-side opening of the NOx gas sensor 10 to the first measurement chamber 159. As such, the first diffusion resistor 116 restricts the introduction amount (passage amount) per unit time of a gas to be measured being introduced into the first measurement chamber 159.

The introduction passage 14 is a region, located on the tip side (left side in FIG. 1) of the first measurement chamber 159, of the space surrounded by the first pump cell 111 and the oxygen partial pressure detection cell 112. The first electrode 135 (covered with the protective layer 122) of the first pump cell 111 and the detection electrode 155 of the oxygen partial pressure detection cell 112 face the first measurement chamber 159.

A second diffusion resistor 117 made of a porous material is disposed on the rear side (right side in FIG. 1) of the first measurement chamber 159, and a second measurement chamber 161 is formed between the third electrode 145 and the second diffusion resistor 117. The second measurement chamber 161 is formed so as to penetrate through the oxygen partial pressure detection cell 112 in the lamination direction.

In addition to the second measurement chamber 161, a reference oxygen chamber 118 is formed inside the NOx gas sensor 10. The reference oxygen chamber 118 is formed between the third solid electrolyte layer 151 of the oxygen partial pressure detection cell 112 and the second solid electrolyte layer 141 of the second pump cell 113. The second measurement chamber 161 and the reference oxygen chamber 118 are arranged in this order in the direction from the rear side to the tip side along the second pump cell 113. A prescribed oxygen concentration (oxygen partial pressure) atmosphere (to serve as a concentration detection reference) is set in the reference oxygen chamber 118.

The reference electrode 157 of the oxygen partial pressure detection cell 112 and the fourth electrode 147 of the second pump cell 113 face the reference oxygen chamber 118.

The heater unit 180 is formed by laminating sheet-like insulating layers 171 and 173 which are made of insulative ceramics such as alumina. The heater unit 180 is provided with a heater 175 which is mainly made of platinum and sandwiched between the insulating layers 171 and 173.

In the NOx gas sensor 10 having the above configuration, the first pump cell 111 can pump oxygen into and out of the first measurement chamber 159. The oxygen partial pressure detection cell 112 can measure the difference between the oxygen partial pressure in the first measurement chamber 159 and the oxygen partial pressure in the reference oxygen chamber 118 which is controlled to a constant value; that is, the oxygen partial pressure detection cell 112 can measure the oxygen partial pressure in the first measurement chamber 159.

The NOx gas sensor 10 is driven by the gas sensor controller 190 which is provided separately. The heater 175 is driven by the gas sensor controller 190, whereby the temperature of each of the first pump cell 111, the second pump cell 113, and the oxygen partial pressure detection cell 112 is increased to an activation temperature.

The gas sensor controller 190, which drives the NOx gas sensor 10, drive-controls the heater 175 so that the temperature of the NOx gas sensor 10 is increased to the activation temperature (e.g., 750° C.). In this state, the gas sensor controller 190 controls a first pump current Ip1 flowing through the first pump cell 111 so that a voltage Vs across the oxygen partial pressure detection cell 112 becomes equal to a preset constant voltage (e.g., 425 mV).

While controlling the first pump current Ip1, the gas sensor controller 190 applies a predetermined second pump voltage Vp2 (e.g., 450 mV) to the second pump cell 113. As a result, in the second measurement chamber 161, NOx is dissociated (reduced) with catalyst action of the pair of second porous electrodes 125 of the second pump cell 113. Resulting oxygen ions move through the second solid electrolyte layer 141 between the third electrode 145 and the fourth electrode 147, whereby a second pump current Ip2 flows. That is, the second pump cell 113 dissociates particular gas components (NOx (nitrogen oxides) to be detected that exist in the second measurement chamber 161 and pumps oxygen from the second measurement chamber 161 to the reference oxygen chamber 118.

Oxygen ions ($O^{2-}$) produced at the third electrode 145 in the second measurement chamber 161 move to the fourth electrode 147 via the second solid electrolyte layer 141, and oxygen molecules ($O_2$) are emitted from the fourth electrode 147.

That is, connected to the NOx gas sensor 10, the gas sensor controller 190 performs processing of adjusting the oxygen concentration in the first measurement chamber 159 through a pumping operation of the first pump cell 111, setting the oxygen concentration in the second measurement chamber 161 to an NOx detection concentration that enables NOx detection, and detecting NOx on the basis of the magnitude, integration value, or the like of the second pump current Ip2.

Figure 2:
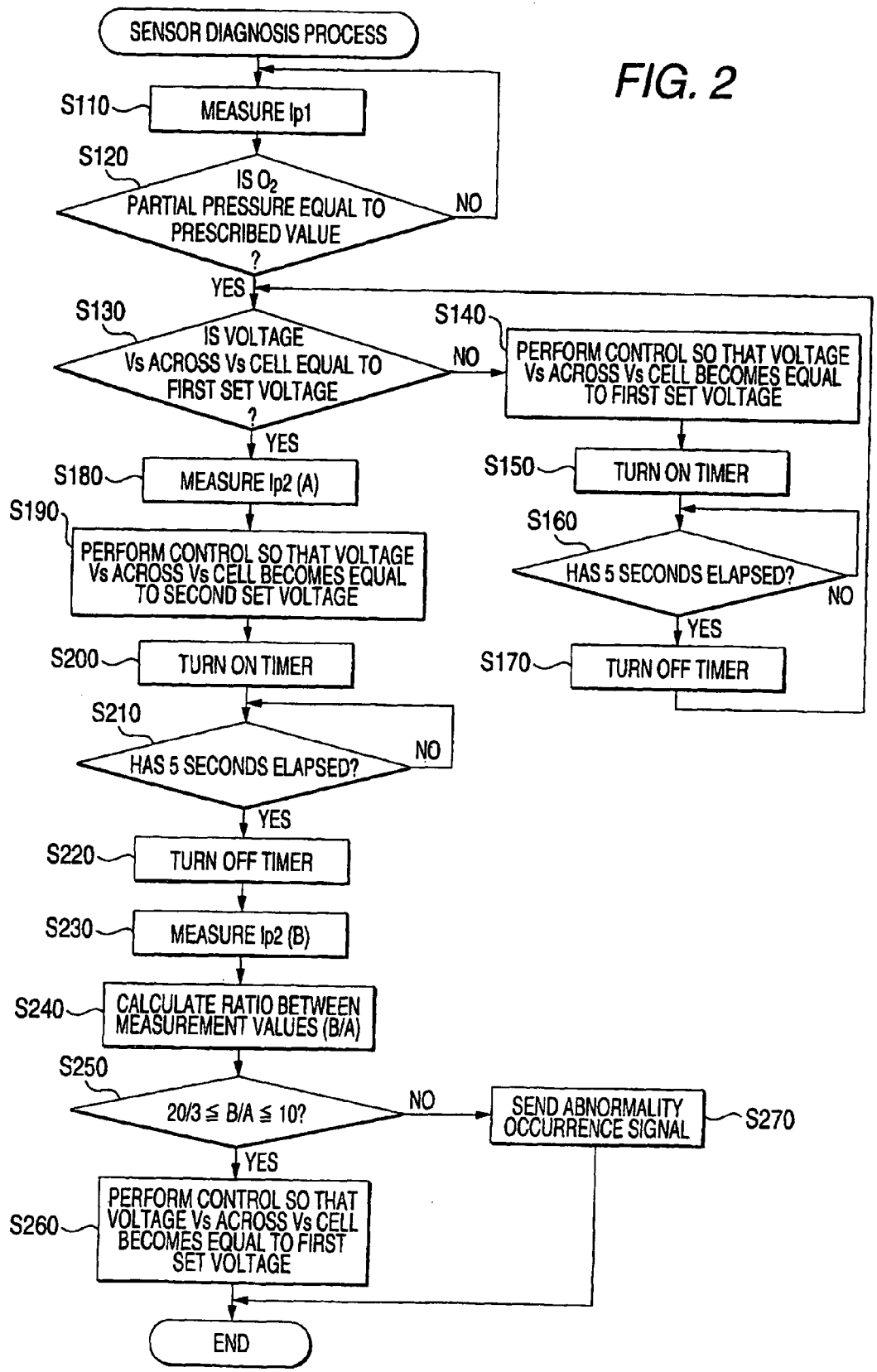
FIG. 2 is a flowchart of a sensor diagnosis process.

Next, the details of a sensor diagnosis process (on-board diagnosis (OBD)) which is executed by the gas sensor controller 190 will be described. FIG. 2 is a flowchart showing the details of the sensor diagnosis process.

It is desirable that the sensor diagnosis process be executed with such timing that the oxygen concentration in an exhaust gas is high, such as immediately after a start of the gas sensor controller 190 or during a fuel-cut operation.

In the sensor diagnosis process shown in FIG. 2, first, at step S110, a current is caused to flow through the first pump cell 111 so that the voltage Vs across the oxygen partial pressure detection cell 112 becomes equal to a preset constant voltage. In this state, an oxygen partial pressure is measured by detecting a first pump current Ip1 flowing through the first pump cell 111.

At step S120, it is judged whether or not the oxygen partial pressure of the gas to be measured is equal to a prescribed value (e.g., 20% which is approximately equal to the oxygen partial pressure of the atmosphere). If it is judged that the oxygen partial pressure of the gas to be measured is equal to the prescribed value, the process moves step S130. If it is judged that the oxygen partial pressure of the gas to be measured is not equal to the prescribed value, the process returns to step S110.

The reason why it is judged at step S120 whether or not the oxygen partial pressure of the gas to be measured is equal to the prescribed value is to execute the process concerned (sensor diagnosis process) in a state that a particular gas such as NOx does not exist in the first measurement chamber 159. If this process were executed in a state that the particular gas such as NOx exists in the first measurement chamber 159, the particular gas such as NOx would be dissociated in the second measurement chamber 161 (second pump cell 113) and judgments in this process might result in an error.

At step S130, it is judged whether or not the voltage Vs across the oxygen partial pressure detection cell (Vs cell) 112 (i.e., the voltage between the detection electrode 155 and the reference electrode 157) is equal to a first set voltage (e.g., 425 mV). If it is judged that the voltage Vs across the oxygen partial pressure detection cell 112 is equal to the first set voltage, the process moves to step S180. If it is judged that the voltage Vs across the oxygen partial pressure detection cell 112 is not equal to the first set voltage, the process moves to step S140.

At step S140, the current flowing through the first pump cell 111 is controlled so that the voltage Vs across the oxygen partial pressure detection cell 112 becomes equal to the first set voltage. Then, the process moves to step S150.

At step S150, a timer that is built in the gas sensor controller 190 is turned on. Then, the process moves to step S160.

At step S160, it is judged whether or not a prescribed time (in this embodiment, 5 s) that the oxygen partial pressure in the second measurement chamber 161 takes to become equal to that in the first measurement chamber 159 has elapsed since the turning-on of the timer. If the prescribed time has elapsed, the process moves to step S170. If the prescribed time has not elapsed yet, step S160 is executed again.

At step S170, the timer which is built in the gas sensor controller 190 is turned off. Then, the process returns to step S130.

On the other hand, at step S180, a current flowing between the two terminals (i.e., the third electrode 145 and the fourth electrode 147) of the second pump cell 113 is measured.

At step S190, the current flowing through the first pump cell 111 is controlled so that the voltage Vs across the oxygen partial pressure detection cell 112 becomes equal to a second set voltage which is lower than the first set voltage. Then, the process moves to step S200. Since the voltage Vs across the oxygen partial pressure detection cell 112 is made equal to the second set voltage which is lower than the first set voltage, the oxygen partial pressure in the first measurement chamber 159 is made higher. In this embodiment, the second set voltage is 50 mV lower than the first set voltage and hence is equal to 375 mV, for example.

At step S200, the timer which is built in the gas sensor controller 190 is turned on. Then, the process moves to step S210.

At step S210, it is judged whether or not a prescribed time (in this embodiment, 5 s) that the oxygen partial pressure in the second measurement chamber 161 takes to become equal to that in the first measurement chamber 159 has elapsed since the turning-on of the timer. If the prescribed time has elapsed, the process moves to step S220. If the prescribed time has not elapsed yet, step S210 is executed again.

At step S220, the timer which is built in the gas sensor controller 190 is turned off. Then, the process moves to step S230.

At step S230, a current flowing between the two terminals of the second pump cell 113 is measured again.

At step S240, the ratio B/A of the current B measured in the second pump cell 113 at step S230 to the current A measured in the second pump cell 113 at step S180 is calculated.

At step S250, it is judged whether or not the ratio B/A falls within a prescribed allowable range which is stored in the gas sensor controller 190. If the ratio B/A falls within the allowable range, the second pump cell 113 is judged normal and the process moves to step S260. If the ratio B/A is out of the allowable range, the second pump cell 113 is judged deteriorated and the process moves to step S270.

At step S260, the current flowing through the first pump cell 111 is controlled so that the voltage Vs across the oxygen partial pressure detection cell 112 becomes equal to the first set voltage (i.e., an ordinary detection state is established). Then, the sensor diagnosis process is finished.

At step S270, an abnormality occurrence signal indicating that the NOx gas sensor 10 is deteriorated is sent to an abnormality notification device provided in the vehicle such as a display control device or an alarm sound generation device. Then, the sensor diagnosis process is finished.

Figure 3:
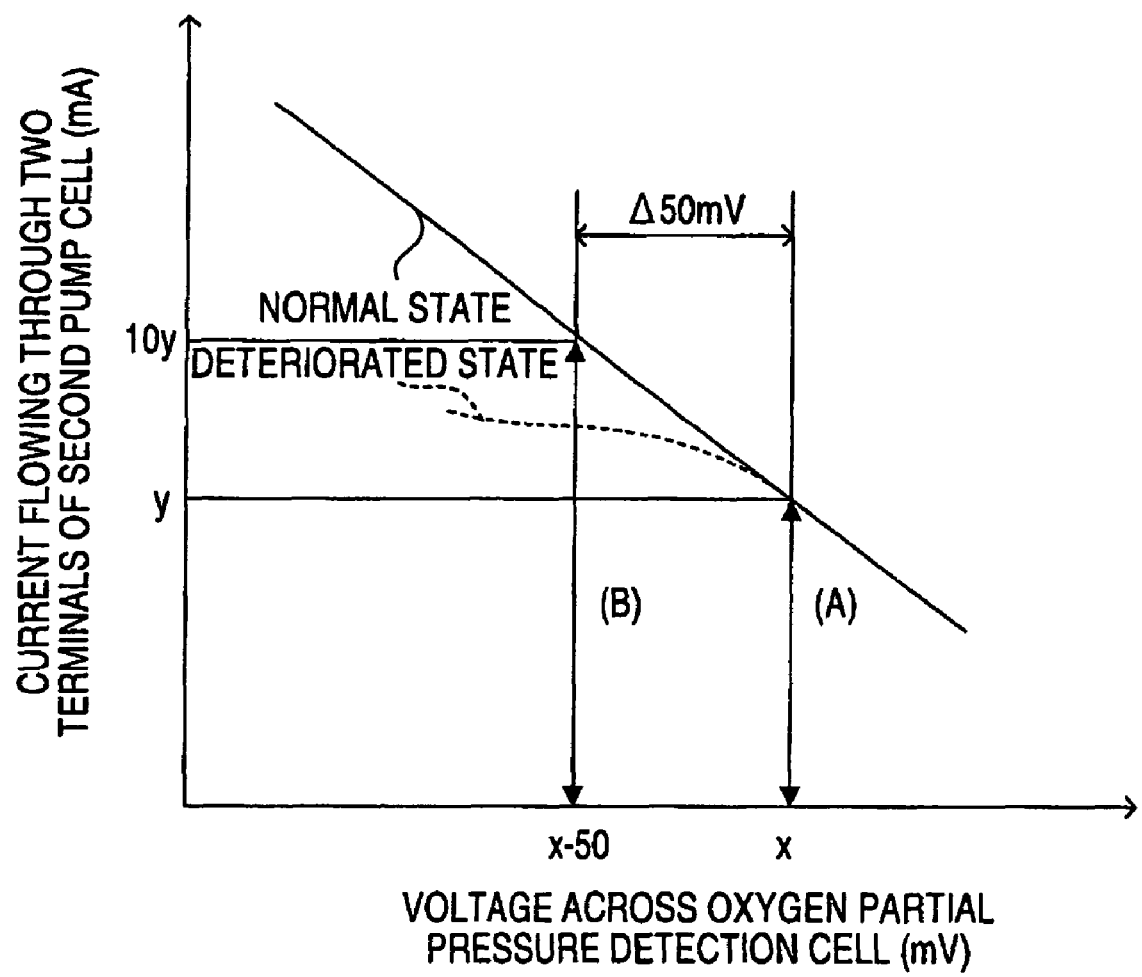
FIG. 3 is a graph showing a relationship between the voltage Vs across an oxygen partial pressure detection cell and the current flowing between the two terminals of a second pump cell.

The current A measured in the second pump cell 113 at step S180 and the current B measured in the second pump cell 113 at step S230 have a relationship shown in FIG. 3. FIG. 3 is a graph showing a relationship between the voltage Vs across the oxygen partial pressure detection cell 112 and the current flowing between the two terminals of the second pump cell 113.

As seen from FIG. 3, the second pump cell 113 being in a normal state has a characteristic that when the voltage Vs across the oxygen partial pressure detection cell 112 is decreased by 50 mV the current flowing between the two terminals of the second pump cell 113 is increased by a factor of 10 (solid line in FIG. 3).

However, in the second pump cell 113 being in a deteriorated state, even if the voltage Vs across the oxygen partial pressure detection cell 112 is decreased by 50 mV, the current flowing between the two terminals of the second pump cell 113 is increased by only a factor that is much smaller than 10 (broken line in FIG. 3).

Utilizing the above phenomenon, in this embodiment, the allowable range is set in advance for the ratio between current values measured at steps S180 and S230 and whether the second pump cell 113 is in a normal state is judged on the basis of whether or not the ratio between current values falls within the allowable range.

More specifically, the prescribed allowable range which is used at step S250 in the embodiment is $20/3 \leq B/A \leq 10$, for example. The reason why the upper limit of the allowable range is set at 10 is that in this embodiment the second pump cell 113 has the characteristic that when the voltage Vs across the oxygen partial pressure detection cell 112 is decreased by 50 mV the current flowing between the two terminals of the second pump cell 113 is increased by a factor of 10. The reason why the lower limit of the allowable range is set at 20/3 (i.e., the upper limit 10 divided by 1.5) is that deterioration detection in vehicular catalyst converters etc. generally employs a judgment reference value that is 1.5 times a restriction value.

As described above in detail, the NOx gas sensor 10 is equipped with the first measurement chamber 159, the first pump cell 111, the second measurement chamber 161, the second pump cell 113, the reference oxygen chamber 118, and the oxygen partial pressure detection cell 112.

And the gas sensor controller 190 executes the sensor diagnosis process to judge whether the NOx gas sensor 10 is in a deteriorated state. That is, in the sensor diagnosis process, the gas sensor controller 190 performs the processing of changing the oxygen partial pressure in the second measurement chamber 161 by changing the oxygen partial pressure in the first measurement chamber 159 (S190), the processing of detecting a current flowing through the second pump cell 113 before the change of the oxygen partial pressure (S180), and the processing of detecting a current flowing through the second pump cell 113 after the change of the oxygen partial pressure (S230).

In the sensor diagnosis process, the gas sensor controller 190 further performs the processing of judging whether or not the ratio between the current values detected by the respective current detecting unit falls within the preset range, judging that the second pump cell 113 is in a normal state if the ratio between the current values falls within the allowable range, and judges that the second pump cell 113 is in a deteriorated state if the ratio between the current values is out of the allowable range (S240 and S250).

Therefore, according to the sensor diagnosis process which is executed by the above-described gas sensor controller 190, whether or not the second pump cell 113 is in a deteriorated state can be judged because if the second pump cell 113 is in a deteriorated state the current flowing through it after a change of the oxygen partial pressure is smaller than in a normal-state value. Therefore, whether the NOx gas sensor 10 having the various cells is in a deteriorated state can be judged.

In the sensor diagnosis process (S190), the gas sensor controller 190 changes the oxygen partial pressure in the second measurement chamber 161 by changing the amount per unit time by which oxygen is pumped in or out by the first pump cell 111.

That is, in the sensor diagnosis process (S190) the gas sensor controller 190 changes the oxygen partial pressure in the second measurement chamber 161 using the first pump cell 111. Therefore, the gas sensor controller 190 can change the oxygen partial pressure in the second measurement chamber 161 without the need for providing the NOx gas sensor 10 with a new oxygen pump cell for changing the oxygen partial pressure. Therefore, the structure for changing the oxygen partial pressure can be simplified.

In the sensor diagnosis process (S230), the gas sensor controller 190 detects a current value after the stabilization standby time (which is necessary for stabilization of the oxygen partial pressure in the second measurement chamber 161) has elapsed after the oxygen partial pressure is changed (S200-S220).

After the stabilization standby time has elapsed since a change of the oxygen partial pressure, the oxygen partial pressure in the second measurement chamber 161 can reliably be set equivalent to that in the first measurement chamber 159. Therefore, whether or not the second pump cell 113 is in a deteriorated state can be judged with higher accuracy by the sensor diagnosis process (S240 and S250).

Capable of judging, with higher accuracy, whether or not the second pump cell 113 is in a deteriorated state, the sensor diagnosis process which is executed by the gas sensor controller 190 can increase the judgment accuracy in judging whether the NOx gas sensor 10 is in a deteriorated state.

The first pump cell 111 and the second pump cell 113 in the embodiment correspond to the above-mentioned terms "first oxygen ion pump cell" and "second oxygen ion pump cell", respectively. The first diffusion resistor 116 and the second diffusion resistor 117 correspond to the above-mentioned terms "first diffusion resistor portion" and "second diffusion resistor portion", respectively. The gas sensor controller 190 corresponds to the above-mentioned term "sensor deterioration judging apparatus".

The sensor diagnosis process of the embodiment corresponds to the term "sensor deterioration judging method." In the sensor diagnosis process, the gas sensor controller 190 executing step S180 corresponds to the above-mentioned term "first current detecting unit" and the gas sensor controller 190 executing step S190 corresponds to the above-mentioned term "oxygen partial pressure changing unit". In the sensor diagnosis process of the embodiment, the gas sensor controller 190 executing step S230 corresponds to the above-mentioned term "second current detecting unit" and the gas sensor controller 190 executing steps S240 and S250 corresponds to the above-mentioned term "deterioration judging unit".

The invention is not limited to the above embodiment at all and it goes without saying that various modifications are possible without departing from the technical scope of the invention.

For example, although the sensor diagnosis process of the embodiment is executed in a state that the particular gas such as NOx does not exist by judging, at steps S110 and S120, whether or not the oxygen partial pressure in a gas to be measured is equal to the prescribed value, steps S110 and S120 are not indispensable. Steps S110 and S120 may be omitted in the case where the influence of the particular gas is negligible in judging, at step S250, whether or not the ratio between current values measured at steps S180 and S230 falls within the allowable range, as in the case where the amount of the particular gas contained in a gas to be measured is slight.

It goes without saying that the numerical values of the oxygen partial pressure (20%) used at step S120 and the standby time (5 s) used at steps S160 and S210 may be set as desired.

This application is based on Japanese Patent Application JP 2005-340536, filed Nov. 25, 2005, the entire content of which is hereby incorporated by reference, the same as if set forth at length.

What is claimed is:

1. A sensor deterioration judging apparatus for judging whether a gas sensor is in a deteriorated state, the gas sensor including:

a first measurement chamber into which a gas to be measured is introduced through a first diffusion resistor portion;

a first oxygen ion pump cell having a first oxygen ion conductor and first and second electrodes provided on the first oxygen ion conductor wherein the first electrode is arranged in the first measurement chamber which pumps oxygen into or out of the gas that has been introduced into the first measurement chamber to be measured;

a second measurement chamber in which the gas to be measured is introduced through a second diffusion resistor portion after being subjected to oxygen pumping in the first measurement chamber;

a second oxygen ion pump cell having a second oxygen ion conductor and third and fourth electrodes provided on the second oxygen ion conductor wherein the third electrode is arranged in the second measurement chamber so that a current corresponding to a concentration of the gas to be measured in the second measurement chamber flows in the second oxygen ion pump cell;

a reference oxygen chamber set to have a reference oxygen partial pressure atmosphere; and an oxygen partial pressure detection cell having a third oxygen ion conductor and fifth and sixth electrodes provided on the third oxygen ion conductor so that the fifth electrode is provided in the first measurement chamber and the sixth electrode is provided in the reference oxygen chamber, the sensor deterioration judging apparatus comprising:
- an oxygen partial pressure changing unit for changing an oxygen partial pressure in the second measurement chamber by changing an oxygen partial pressure in the first measurement chamber;
- a first pump current detecting unit for detecting a current flowing through the second oxygen ion pump cell before the oxygen pressure changing unit changes the oxygen partial pressure;
- a second pump current detecting unit for detecting a current flowing through the second oxygen ion pump cell after the oxygen pressure changing unit changes the oxygen partial pressure; and
- a deterioration judging unit for judging that the second oxygen ion pump cell is in a deteriorated state when a ratio between the currents detected by the first and second current detecting unit is out of a preset range;

the oxygen partial pressure of the gas to be measured in the first measurement chamber, which is measured based on the current flowing in the first oxygen ion pump cell, is determined whether or not the oxygen partial pressure is a predetermined value, and wherein the oxygen partial pressure changing unit changes the oxygen partial pressure in the first measurement chamber when the oxygen partial pressure is determined as the predetermined value.

2. The sensor deterioration judging apparatus as claimed in claim 1, wherein the oxygen partial pressure changing unit changes the oxygen partial pressure in the second measurement chamber by changing an amount per unit time by which oxygen is pumped in or out by the first oxygen ion pump.

3. The sensor deterioration judging apparatus as claimed in claim 1, wherein the second current detecting unit detects a current after a stabilization standby time has elapsed after the oxygen partial pressure changing unit changes the oxygen partial pressure in the first measurement chamber.

4. The sensor deterioration judging apparatus as claimed in claim 2, wherein the second current detecting unit detects a current after a stabilization standby time has elapsed after the oxygen partial pressure changing unit changes the oxygen partial pressure in the first measurement chamber.

5. A sensor deterioration judging method for judging whether a gas sensor is in a deteriorated state, the gas sensor including:

a first measurement chamber into which a gas to be measured is introduced through a first diffusion resistor portion;

a first oxygen ion pump cell having a first oxygen ion conductor and first and second electrodes arranged on the first oxygen ion conductor wherein the first electrode is provided in the first measurement chamber;

a second measurement chamber in which the gas to be measured is introduced through a second diffusion resistor portion after being subjected to oxygen pumping in the first measurement chamber;

a second oxygen ion pump cell having a second oxygen ion conductor and third and fourth electrodes provided on the second oxygen ion conductor wherein the third electrode is provided in the second measurement chamber so that a current corresponding to a concentration of the gas to be measured in the second measurement chamber flows in the second oxygen ion pump cell;

a reference oxygen chamber set to have a reference oxygen partial pressure atmosphere; and an oxygen partial pressure detection cell having a third oxygen ion conductor and fifth and sixth electrodes provided on the third oxygen ion conductor so that the fifth electrode is provided in the first measurement chamber and the sixth electrode is provided in the reference oxygen chamber, the sensor deterioration judging method comprising:
- detecting a current flowing through the second oxygen ion pump cell;
- changing an oxygen partial pressure in the second measurement chamber by changing an oxygen partial pressure in the first measurement chamber;
- detecting a current flowing through the second oxygen ion pump cell again after the change of the oxygen partial pressure in the first measurement chamber; and
- judging that the second oxygen ion pump cell is in a deteriorated state in case a ratio between the detected currents is out of a preset range;

the oxygen partial pressure of the gas to be measured in the first measurement chamber, which is measured based on the current flowing in the first oxygen ion pump cell, is determined whether or not the oxygen partial pressure is a predetermined value, and wherein the oxygen partial pressure changing unit changes the oxygen partial pressure in the first measurement chamber when the oxygen partial pressure is determined as the predetermined value.

* * * * *